(12) United States Patent
Tokieda

(10) Patent No.: US 7,724,356 B2
(45) Date of Patent: May 25, 2010

(54) APPARATUS FOR MEASURING DIFFERENTIAL REFRACTIVE INDEX

(75) Inventor: Tsunemi Tokieda, Yokohama (JP)

(73) Assignee: Showa Denko K.K., Tokyo (JP)

( * ) Notice: Subject to any disclaimer, the term of this patent is extended or adjusted under 35 U.S.C. 154(b) by 373 days.

(21) Appl. No.: 11/913,621

(22) PCT Filed: May 11, 2006

(86) PCT No.: PCT/JP2006/309871

§ 371 (c)(1),
(2), (4) Date: Nov. 5, 2007

(87) PCT Pub. No.: WO2006/121195

PCT Pub. Date: Nov. 16, 2006

(65) Prior Publication Data

US 2009/0079968 A1 Mar. 26, 2009

(30) Foreign Application Priority Data

May 13, 2005 (JP) ............................. 2005-141696

(51) Int. Cl.
*G01N 21/41* (2006.01)
(52) U.S. Cl. .................. 356/130; 356/128; 356/432
(58) Field of Classification Search ......... 356/128–137, 356/317, 432–444; 250/573, 574, 575, 576; 73/61.52

See application file for complete search history.

(56) References Cited

U.S. PATENT DOCUMENTS

| | | | |
|---|---|---|---|
| 2,612,814 A | 10/1952 | Glasser | |
| 2,800,053 A | 7/1957 | Svensson | |
| 3,539,263 A | 11/1970 | Waters | |
| 3,612,697 A | 10/1971 | Nebe | |
| 5,157,454 A | 10/1992 | Oka et al. | |
| 5,168,325 A * | 12/1992 | Yoder-Short | 356/517 |
| 5,389,524 A * | 2/1995 | Larsen et al. | 435/29 |
| 5,398,110 A * | 3/1995 | Kitaoka | 356/130 |
| 6,094,262 A * | 7/2000 | Almeida et al. | 356/130 |
| 6,130,439 A * | 10/2000 | Le Menn | 250/573 |
| 6,295,125 B1 * | 9/2001 | Tokieda et al. | 356/130 |
| 7,382,461 B2 * | 6/2008 | Kimura | 356/445 |
| 2005/0195392 A1 * | 9/2005 | Uchimura et al. | 356/246 |

FOREIGN PATENT DOCUMENTS

| | | |
|---|---|---|
| JP | 46-2800 | 10/1971 |
| JP | 3-170847 A | 7/1991 |
| JP | 11132944 A * | 5/1999 |

* cited by examiner

*Primary Examiner*—Sang Nguyen
(74) *Attorney, Agent, or Firm*—Sughrue Mion, PLLC

(57) ABSTRACT

The invention provides an apparatus for measuring the differential refractive index for liquid chromatography which greatly improves the sensitivity while having quick responsiveness to refractive index difference of sample liquid, as well as a differential refractive index detector and a measurement method for a differential refractive index using the same. The apparatus for measuring a differential refractive index having a flow cell deflecting a measurement beam in accordance with the refractive index difference between a reference liquid and a sample liquid for measuring the change of the deflection angle on the basis of the refractive index difference of the measurement beam transmitted between the reference liquid and the sample liquid, wherein the flow cell comprises three independent chambers including a first chamber, a second chamber adjacent to the first chamber and a third chamber adjacent to the second chamber.

6 Claims, 8 Drawing Sheets

FIG. 1A
FIG. 1B
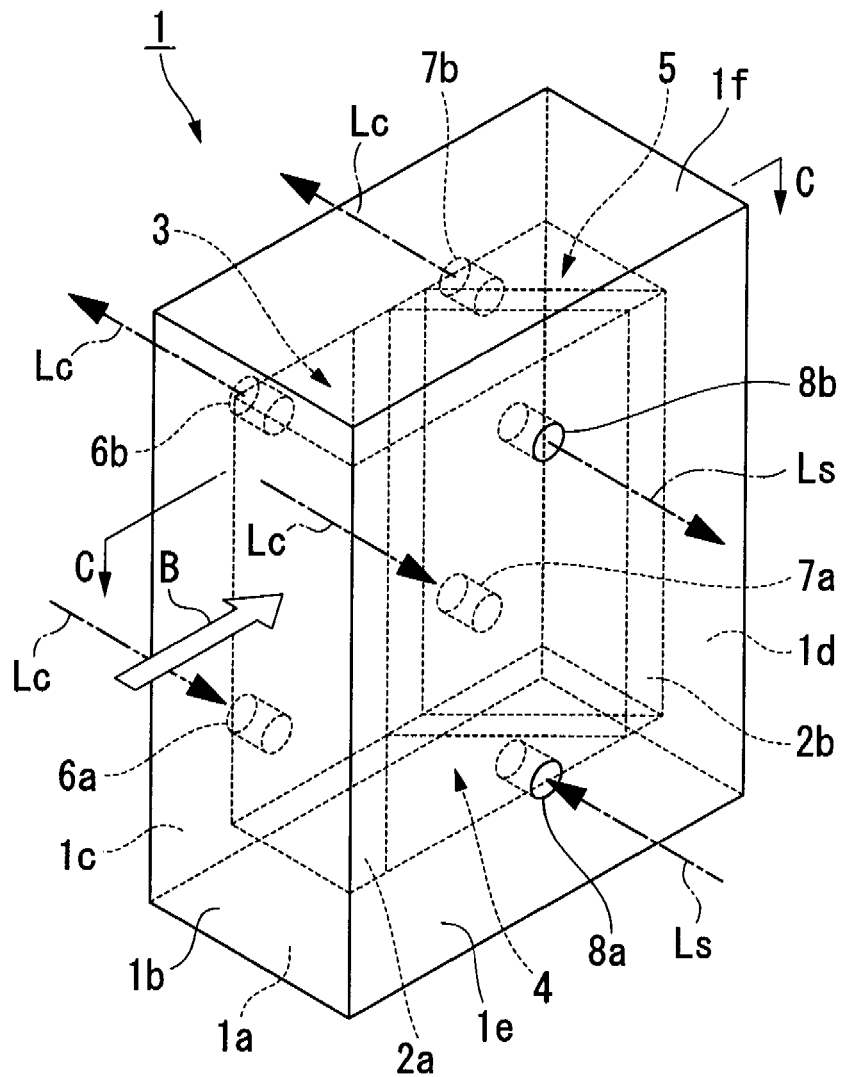
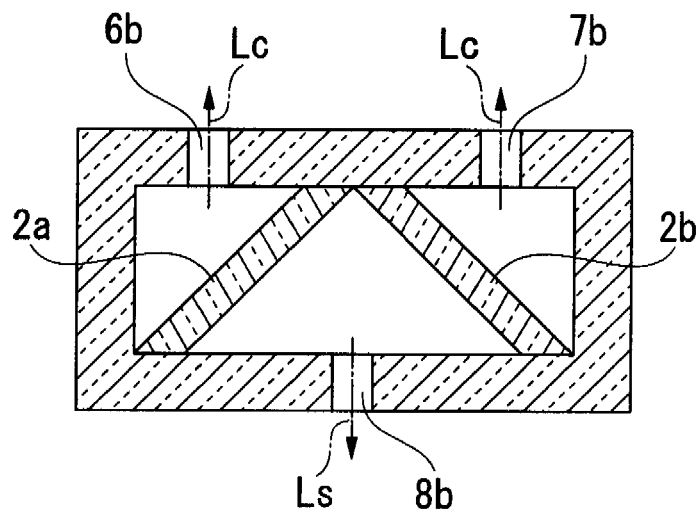

APPARATUS FOR MEASURING DIFFERENTIAL REFRACTIVE INDEX

CROSS REFERENCE TO RELATED APPLICATIONS

Priority is claimed on Japanese Patent Application No. 2005-141696, filed May 13, 2005.

TECHNICAL FIELD

The present invention relates to an apparatus for measuring a differential refractive index by measuring the change of deflection angle on the basis of the refractive index difference between the reference liquid and the sample liquid, as well as relates to a differential refractive index detector and a measurement method for a differential refractive index using the same.

BACKGROUND ART

A deflection-type differential refractive index detector for a liquid chromatograph has a quadrangular prism flow cell 100 constructed from two triangular prism chambers 100a and 100b as shown in FIG. 11A. The flow cell 100 has a partition plate 101 partitioning the two chambers 100a and 100b.

A measurement beam B' is irradiated on the flow cell 100 so as to sequentially transmit the two chambers of 100a for filling with or passage of the reference liquid Lc' and 100b for filling with or passage of the a sample liquid Ls'. At this time, the flow cell 100 deflects the measurement beam B' in accordance with the refractive index difference of the measurement beam B' between the reference liquid Lc' and the sample liquid Ls', as shown in FIG. 11B. A change in the deflection angle is detected as the positional change of the measurement beam by a photodetector (non-illustrated) in a position apart from the flow cell 100 at a predetermined distance on the basis of the refractive index difference between the reference liquid Lc' and the sample liquid Ls' in the flow cell 100.

The deflection angle of the measurement beam B' with the same refractive index difference is dependent on the angle between the optical axis of the measurement beam B' and the partition plate 101, therefore the angle of the partition plate 101 is usually set to 45° to the optical axis of the measurement beam B' so as to obtain a maximum sensitivity.

In the deflection-type differential refractive index detector, a sensitivity to the differential refractive index can be increased by extending the distance from the flow cell 100 to the photodetector. However, if the distance from the flow cell 100 to the photodetector is extended, not only drift increases due to distortion of the optical bench and the increase of temperature distribution, but also the device becomes too large. As a result, the method can not improve the overall performance. Namely, the method of extending the distance from the flow cell to the photodetector can not improve the signal/noise (S/N) ratio, even if improving the circuits of the photodetector.

A method of increasing the sensitivity by deflecting a beam twice has been proposed (e.g., see Patent references 1, 2) in the deflection-type differential refractive index detector.

For example, Patent Reference 1 described a construction in which two triangular prism chambers communicate with each other in the longitudinal side and a sample liquid flows from one chamber to the other chamber through the communication section. However, in the case of the construction described in Patent Reference 1, it needed more time to substitute the sample liquid in the chambers by flowing, because the flow passage is complicated, resulting in problem that a quick response to the inflow liquid change cannot be obtained. When a reference liquid flows or is sealed in a flow passage where a sample liquid flowed, or a sample liquid flows into a hollow prism where a reference liquid flowed or was sealed, there also is the problem that a quick substitution of a reference liquid cannot be made.

On the other hand, a deflection-type differential refractive index detector using two measurement beams has been described in Patent Reference 2. However, in the case of the construction described in the Patent Reference 2, it need more time to substitute the liquid in a section sandwiched by the two triangular prism chambers because they become a pentagonal prism (rough the shape of an M) with a large volume. Accordingly, when such a cell are used as a flow cell of a differential refractive index detector for liquid chromatography, there is the problem that they are not resistant to use from the viewpoint of responsiveness of the concentration change of a sample liquid and liquid replacement of a reference liquid.

Patent reference 1: Japanese Laid-Open Patent Application S46-2800 (FIG. 1)

Patent reference 2: Japanese Laid-Open Patent Application H3-170847 (FIG. 7)

DISCLOSURE OF INVENTION

The present invention was made in view of such a situation and aims at providing an apparatus for measuring the differential refractive index that greatly improves the sensitivity while having quick responsiveness to a refractive index change of a sample liquid, as well as a differential refractive index detector and a measurement method for a differential refractive index using the same.

The present invention provides the following aspects.

(1) An apparatus for measuring a differential refractive index having a flow cell deflecting a measurement beam in accordance with the refractive index difference between a reference liquid and a sample liquid for measuring the change of the deflection angle on the basis of the refractive index difference of the measurement beam transmitted between the reference liquid and the sample liquid, wherein the flow cell comprises three independent chambers including a first chamber, a second chamber adjacent to the first chamber and a third chamber adjacent to the second chamber, and the measurement beam is irradiated on the flow cell so as to sequentially transmit these three chambers in a state in which the reference liquid flows or is sealed in the first and third chambers and in a state in which the sample liquid flows or is sealed in the second chamber.

(2) An apparatus for measuring the differential refractive index according to (1), wherein the flow cell is rough quadrangular prism and the first to third chambers are rough triangular prism.

(3) An apparatus for measuring the differential refractive index according to (1) or (2), wherein the flow cell has a first partition plate for partition between the first chamber and the second chamber and a second partition plate for partition between the second chamber and the third chamber, and the first partition plate and the second partition plate are arranged perpendicular to each other and each of the plates has an angle of 45±1° relative to a optical axis of the measurement beam.

(4) An apparatus for measuring the differential refractive index according to any of (1) to (3), further comprises a flow passage which allows the reference liquid to flow from the first chamber to the third chamber.

(5) An apparatus for measuring the differential refractive index according to (4), further comprises a first sealing plate forming the flow passages and a first block, wherein the first sealing plate is sandwiched between the first block and the flow cell.

(6) An apparatus for measuring the differential refractive index according to (5), wherein the flow cell further comprises a first inflow port allowing the reference liquid to flow into the first chamber, a first outflow port allowing the reference liquid to flow out from the first chamber, a second inflow port allowing the sample liquid to flow into the second chamber, a second outflow port allowing the sample liquid to flow out from the second chamber, a third inflow port allowing the reference liquid to flow into the third chamber, and a third outflow port allowing the reference liquid to flow out from the third chamber, wherein, the first sealing plate comprises a reference-side inflow hole and a reference-side outflow hole in positions corresponding to the first inflow port and the third outflow port, the first block comprises a reference-side inflow passage and a reference-side outflow passage at positions corresponding to the reference-side inflow hole and the reference-side outflow hole, and the flow passage is formed between the first outflow port and the third inflow port.

(7) An apparatus for measuring the differential refractive index according to (6), further comprises a second sealing plate having a sample-side inflow hole and a sample-side outflow hole at positions corresponding to the second inflow port and the second outflow port, and a second block having a sample-side inflow passage and a sample-side outflow passage in positions corresponding to the sample-side inflow hole and the sample-side outflow hole, wherein the second sealing plate is sandwiched between the second block and the flow cell.

(8) A differential refractive index detector, comprising an apparatus for measuring the differential refractive index according to any of (1) to (7), a light emitting device emitting a measurement beam on the apparatus for measuring the differential refractive index, and a photo-detection device detecting the measurement beam that transmits the apparatus for measuring the differential refractive index.

(9) A differential refractive index detector according to (8), further comprises a light reflection device that reflects the measurement beam emitted by the light emitting device and transmitting the flow cell in the order of the first, second and third chambers so as to transmit the flow cell in the order of the third, second and first chambers, wherein the photo-detection device detects measurement beam reflected by the light reflection device and transmitted through the flow cell.

(10) A method for measuring the differential refractive index using the apparatus for measuring the differential refractive index according to any of the (1) to (7), comprises sealing or making flowing the reference liquid in the first and third chambers, sealing or making flowing the sample liquid flows in the second chamber, irradiating a measurement beam on the flow cell so as to sequentially transmit the three chambers, and measuring a change of the deflection angle on the basis of a refractive index difference of the measurement beam transmitted the flow cell between the reference liquid and the sample liquid.

BRIEF DESCRIPTION OF THE DRAWINGS

FIG. 1A is an oblique view showing structure of flow cell according to the present invention.

FIG. 1B is a cross-section view showing structure of flow cell in FIG. 1A.

BEST MODE FOR CARRYING OUT THE INVENTION

Figure 2:
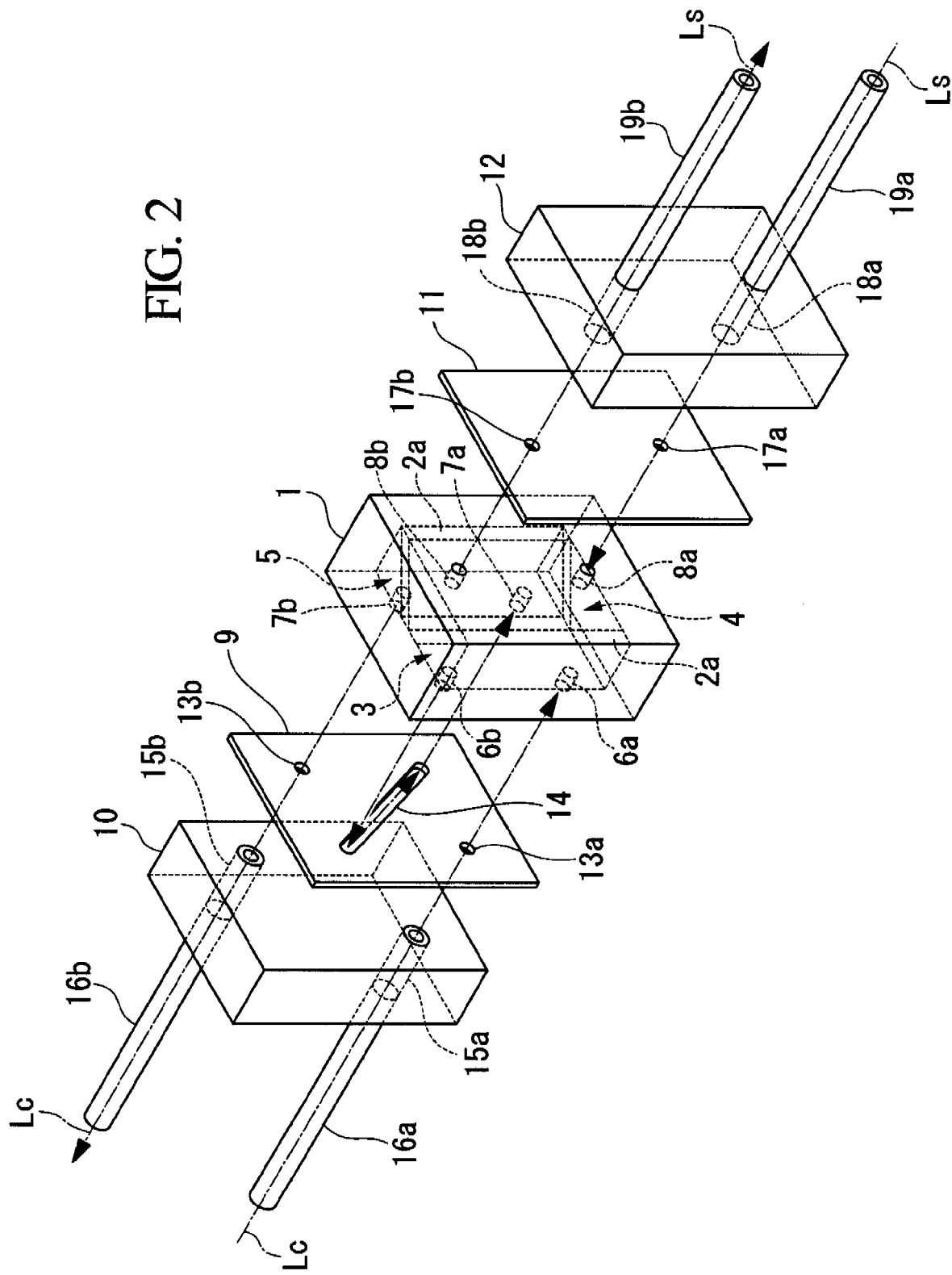
FIG. 2 is an exploded oblique view showing structure of sealing plates and blocks mounted to flow cell shown in FIG. 1.

An apparatus for measuring the differential refractive index applied with the present invention as well as a differential refractive index detector and a measurement method for the differential refractive index using the same are described in detail hereafter, with reference to the following drawings.

First, an apparatus for measuring the differential refractive index applied with the present invention is described.

The apparatus for measuring the differential refractive index applied with the present invention has a flow cell 1 as shown in FIG. 1A and FIG. 1B, and is suitable to be used in a deflection-type differential refractive index detector for a liquid chromatograph that measures the change of deflection angle on the basis of a refractive index difference between a reference liquid (reference liquid) Lc and a sample liquid (sample liquid) Ls in the flow cell 1.

More specifically, the whole of the flow cell 1 is made in a rough quadrangular prism shape by jointing transparent parallel-plane plates of quartz glass, etc. by abutting mutual jointing surfaces. A rough quadrangular prism internal space is constructed from a bottom plate 1a forming the bottom face, side plates 1b, 1c, 1d, 1e forming four side faces and a ceiling if forming the top face so as to construct the flow cell 1. Moreover, the flow cell 1 constructs three independent rough triangular prism chambers by partitioning the internal space with a first partition plate 2a and a second partition plate 2b, namely, the flow cell 1 constructs a first chamber 3, an second chamber 4 adjacent to the first chamber 3 by the first partition plate 2a, and an third chamber 5 adjacent to the second chamber 4 by the second partition plate 2b.

Two pieces of transparent plates of quartz glass with two parallel surfaces, etc are used as the first partition plate 2a and the second partition plate 2b. The first partition plate 2a is jointed by an abutting joint face on the side plates 1c, 1e so as to partition the inside of flow cell 1 between the central part of side plate 1c and one corner of side plate 1e. On the other hand, the second partition plate 2b is jointed by abutting the joint face to the side plates 1c, 1e so as to partition the inside of flow cell 1 between the central part of side plate 1c and another corner of side plate 1e. Thereby, the first partition plate 2a and the second partition plate 2b are arranged perpendicular to each other and each has an angle of 45±1° to the side plate 1c in a state in which the first partition plate 2a and the second partition plate 2b are abut each other at the central part at the side plate 1c side.

The side plate 1c of flow cell 1 has a first inflow port 6a which allows the reference liquid Lc to inflow into the first chamber 3, a first outflow port 6b which allows the reference liquid Lc to outflow from the first chamber 3, a third inflow port 7a which allows the reference liquid Lc to inflow into the third chamber 5, and a third outflow port 7b which allows the reference liquid Lc to outflow from the third chamber 5. In these ports, the first inflow port 6a and the third inflow port 7a are provided by locating them in the lower part of side plate 1c, and the first outflow port 6b and the third outflow port 7b are provided by locating them in the upper part of side plate 1c. On the other hand, the side plate 1e of flow cell 1 has a second inflow port 8a which allows the sample liquid Ls to inflow into the second chamber 4 and a second outflow port 8b which allows the sample liquid Ls to outflow from the second chamber 4. In these ports, the second inflow port 8a is provided by locating it in the lower part of side plate 1e and the second outflow port 8b is provided by locating it in the upper part of side plate 1e.

As shown in FIG. 2, the apparatus for measuring the differential refractive index is provided with a first sealing plate 9 arranged opposite to the side plate 1c of flow cell 1, a first block 10 making this first sealing plate 9 sandwiched between the first block 10 and the flow cell 1, a second sealing plate 11 arranged opposite to the side plate 1e of flow cell 1, and a second block 12 making the second sealing plate 11 sandwiched between the first block 12 and the flow cell 1.

The first sealing plate 9 is made of, e.g., a fluororesin, etc. This sealing plate 9 has a reference-side inflow hole 13a and a reference-side outflow hole 13b at positions corresponding to the first inflow port 6a and the third outflow port 7b of the flow cell 1. The first sealing plate 9 has a slit 14 guiding the reference liquid Lc outflowing from the first outflow port 6b of above flow cell 1 to the third inflow port 7a. Slit 14 forms a linear passage which allows the reference liquid Lc to flow from the first chamber 3 to the third chamber 5 and is formed obliquely between a position corresponding to the first outflow port 6b and a position corresponding to the third inflow port 7a.

The first block 10, which is made of, e.g., stainless steel, etc., is mounted to the flow cell 1 so as to make the first sealing plate 9 sandwiched between the first block 10 and the side plate 1c of flow cell 1. The first block 10 has a reference-side inflow passage 15a and a reference-side outflow passage 15b at positions corresponding to the reference-side inflow hole 13a and the reference-side outflow hole 13b of the first sealing plate 9. Moreover, a reference-side inflow tube 16a which allows the reference liquid Lc to inflow into the reference-side inflow passage 15a and a reference-side outflow tube 16b which allows the reference liquid Lc to outflow from reference the reference-side outflow passage 15b are mounted to this first block 10 by locating them on the side opposite to the sealing plate 9.

The second sealing plate 11 is made of, e.g., a fluororesin, etc. The second sealing plate 11 has a sample-side inflow hole 17a and a sample-side outflow hole 17b at positions corresponding to the second inflow port 8a and the second outflow port 8b of above flow cell 1.

The second block 12, which is made of, e.g., stainless steel, etc., is mounted to the flow cell 1 so as to sandwich the second sealing plate 11 between the second block 12 and the side plate 1e of flow cell 1. This second block 12 has a sample-side inflow passage 18a and a sample-side outflow passage 18b at positions corresponding to a sample-side inflow hole 17a and a sample-side outflow hole 17b of above second sealing plate 11. Moreover, a sample-side inflow tube 19a which allows the sample liquid Ls to inflow into the sample-side inflow passage 18a and a sample-side outflow tube 19b which allows the sample liquid Ls to outflow from the sample-side outflow passage 18b are mounted to the second block 12 by locating them on the side opposite to the second sealing plate 11.

In the apparatus for measuring the differential refractive index having a structure such as described above, the reference liquid Lc inflows from the reference-side inflow tube 16a into the first chamber 3 through the reference-side inflow hole 13a and the first inflow port 6a. The reference liquid Lc inflowing into the first chamber 3 outflows from the first outflow port 6b and inflows into the third chamber 5 through the slit 14 and the third inflow port 7a. Then, the reference liquid Lc inflowing into the third chamber 5 out-flows from the third outflow port 7b and outflows from the reference-side outflow tube 16b through the reference-side inflow hole 13b and the reference-side outflow passage 15b, as shown below:

Lc:16a→15a→13a→6a→1$^{st}$Chamber3→6b→14→7a→3$^{rd}$Chamber5→7b→13b→15b→16b.

On the other hand, in this measurement tool for the differential refractive index, the sample liquid Ls inflows from the sample-side inflow tube 19a into the second chamber 4 through the sample-side inflow passage 18a of second block 12, the sample-side inflow hole 17a and the second inflow port 8a. Then, the sample liquid Ls inflowing into the second chamber 4 outflows from the second outflow port 8b and outflows from the sample-side outflow tube 19b through the sample-side inflow hole 17b and the sample-side outflow passage 18b, as shown below:

Ls:19a→18a→17a→8a→2$^{nd}$Chamber 4→8b→17b→18b→19b.

In the apparatus for measuring the differential refractive index, if the measurement beam B is irradiated on the flow cell 1 so as to sequentially transmit the three chambers 3, 4, 5 in a state in which the same reference liquid Lc flows or is sealed in the first chamber 3 and the third chamber 5, and the sample liquid Ls flows or is sealed in the second chamber 4, the measurement beam B passing through the flow cell 1 is deflected in accordance with the refractive index difference between the reference liquid Lc and the sample liquid Ls.

The above apparatus of measuring the differential refractive index shows a construction in which the flow passage (slit 14) for the reference liquid Lc to flow from the first chamber 3 to the third chamber 5 is provided in the first sealing plate 9, but it is not necessarily restricted to such a construction. For example, it can also adopt a construction in which such a flow passage is provided in the first block 10. More specifically, a construction in which a reference-side outflow hole and a reference-side inflow hole corresponding to the first outflow port 6b and the third inflow port 7a of above flow cell 1 are provided in the first sealing plate 9, and a groove communicating between the reference-side outflow hole and reference-side inflow hole of first sealing plate 9 is provided in the first block 10.

Next, the differential refractive index detector and the measurement method for the differential refractive index using the above apparatus of measuring the differential refractive index are described.

Figure 3A:
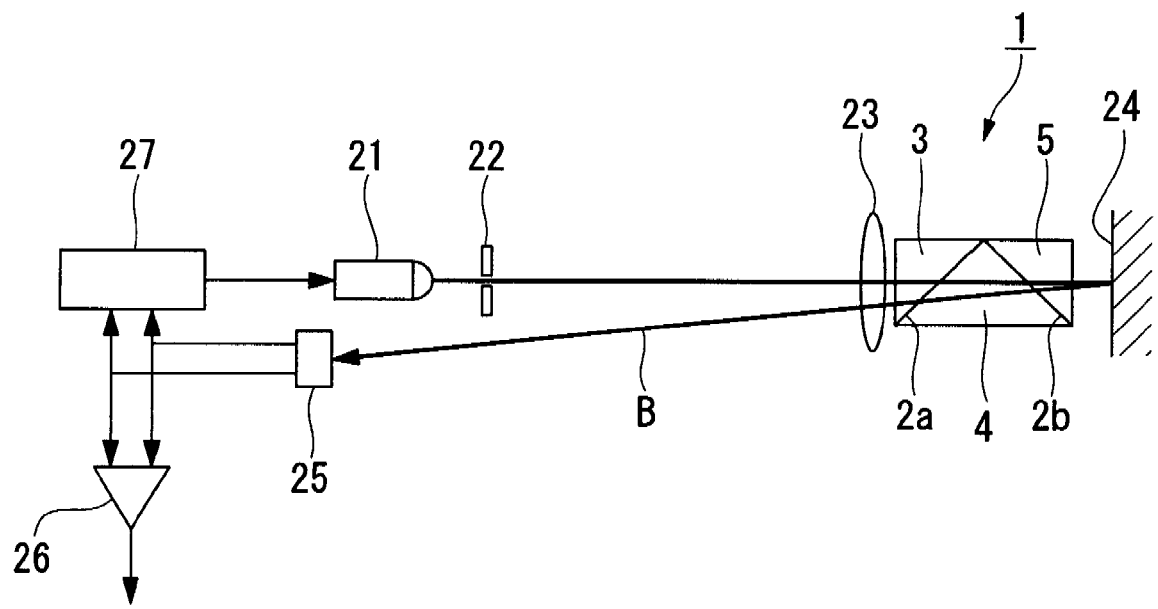
FIG. 3A is a schematic diagram showing construction of a differential refractive index detector using flow cell shown in FIG. 1.
Figure 3B:
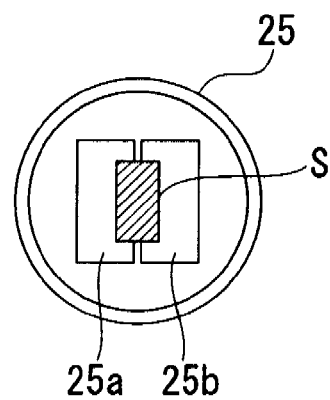
FIG. 3B is a schematic diagram showing a photodetector in a differential refractive index detector using flow cell shown in FIG. 1.

The differential refractive index detector applied with the present invention is a deflection-type differential refractive index detector for liquid chromatograph as shown in, e.g., FIG. 3A and FIG. 3B. More specifically, the differential refractive index detector is provided with a lamp 21 emitting a measurement beam B, a slit 22 through which the measurement beam B emergent from the lamp 21 passes, a collimator lens 23 making the measurement beam B passing through the slit 22 into a parallel light, the above flow cell 1 arranged in the optical path of measurement beam B made into a parallel light by the collimator lens 23, a mirror 24 as a light reflection device for folding the optical path of measurement beam B transmitting this flow cell 1, and a photodetector 25 as a light-detecting device for detecting the measurement beam B reflected by the mirror 24 and transmitting the flow cell 1 again.

The differential refractive index detector is provided with a differential amplifier 26 for detecting the difference between signals of light received by two photodetector surfaces 25a, 25b of the photodetector 25 described later, and a light quantity reference circuit 27 which performs the light quantity reference of lamp 21 so as to keep the light quantity of measurement beam B constant from the sum of signals of light received by two photodetector surfaces 25a, 25b of the photodetector 25. Those which are known can be used as the device for photodetector detection of measurement beam B and device for performing the light reference of measurement beam B.

In the deflection-type differential refractive index detector having a structure such as that described above, the measurement beam B emitted from the lamp 21 passes through the slit 22, made into a parallel light by the collimator lens 23 and is irradiated on the side plate 1b side of flow cell 1. The measurement beam B irradiated on the flow cell 1 transmits the flow cell 1 in the order of the first chamber 3, second chamber 4 and third chamber 5, and exits from the side plate 1d side, and is then reflected and folded by the mirror 24, it reverse transmits the flow cell 1 in the order of the third chamber 5, second chamber 4 and first chamber 3 at this time.

Figure 4:
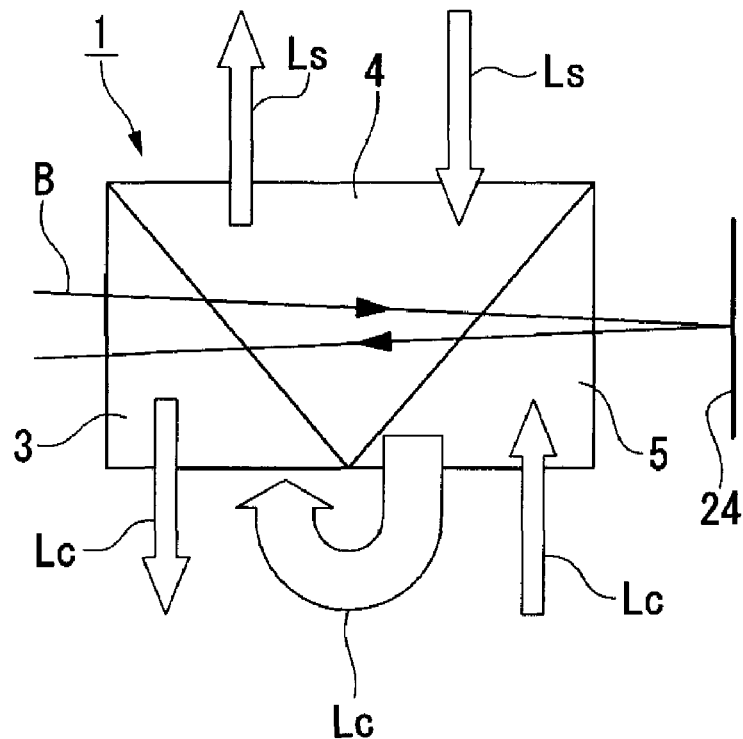
FIG. 4 is a schematic diagram for describing flow of sample liquid and reference liquid in flow cell of present invention.

Here, the first partition plate 2a and the second partition plate 2b are arranged perpendicular to each other and each has an angle of 45±1° relative to the optical axis of measurement beam B. Accordingly, as shown in FIG. 4, the measurement beam B is deflected four times in the same direction in accordance with a refractive index difference between the reference liquid Lc filling up first chamber 3 and third chamber 5 and the sample liquid Ls filling up second chamber 4 while passing through the flow cell 1 twice. Then, as shown in FIG. 3B, an image S of slit 22 was obtained on the photodetector faces 25a, 25b of the photodetector 25, through the deflected measurement beam B.

In the deflection-type differential refractive index detector, the photodetector 25 detects the change of deflection angle as the position change of measurement beam B on the basis of a refractive index difference between the reference liquid Lc and the sample liquid Ls of measurement beam B transmitting the flow cell 1. More specifically, the photodetector 25 has two photosensor surfaces 25a, 25b divided along a dividing line corresponding to a direction parallel to the slit 22, and the position of image of slit 22 focusing on the two receiving faces 25a, 25b changes in proportion to the refractive index difference between the reference liquid Lc and the sample liquid Ls. This position change of image causes a difference of a signal intensity output from the two photosensor faces 25a, 25b, therefore the change of deflection angle can be detected on the basis of the refractive index difference between the reference liquid Lc and the sample liquid Ls by detecting the difference of signals of light received by two photosensor faces 25a, 25b with the differential amplifier 26.

In the differential refractive index detector applied with the present invention, as shown in FIG. 4, the first partition plate 2a and the second partition plate 2b are arranged perpendicular to each other and each has an angle of 45±1° relative to the optical axis of measurement beam B. The sample liquid Ls flows through the second chamber 4 provided between the partition plates 2a, 2b. In this case, the measurement beam B is deflected four times in the same direction in accordance with the refractive index difference between the reference liquid Lc filling up first chamber 3 and third chamber 5 and the sample liquid Ls second chamber 4 while passing through the flow cell 1 twice. Accordingly, in the differential refractive index detector, the sensitivity to the refractive index change of sample liquid Ls can be greatly increased without extending the optical path length of measurement beam B.

In the differential refractive index detector suitable to this invention, the liquid replacement of reference liquid Lc can be quickly performed by providing a flow passage which allows the reference liquid Lc to flow from the first chamber 3 to the third chamber 5 of flow cell 1. On the other hand, in the case of such a flow cell described in the above Patent reference 1, the sample liquid Ls must pass between the first chamber 3 and the third chamber 5 with a complicated flow passage shape as shown by the enclosed area A in FIG. 5, therefore the problem of increasing the spread of peak of chromatogram occurs. (In FIG. 5, same symbols are attached to equal parts as FIG. 4).

Accordingly, in the differential refractive index detector applied with the invention, the liquid replacement properties of reference liquid Lc is improved and responds quickly to the refractive index change of sample liquid Ls, therefore the change of deflection angle can be measured with high sensitivity on the basis of a refractive index difference of reference liquid Lc and sample liquid Ls of the measurement beam B transmitting the flow cell 1.

As described above, the present invention can provide a high-sensitivity apparatus of measuring a differential refractive index which brings a double signal/noise ratio and a reduction of drift while having a quick responsiveness to the refractive index difference change of sample liquid Ls, as well as a differential refractive index detector and a measurement method for differential refractive index using the same.

EXAMPLES

The present invention is clarified by the Examples below.

Figure 6:
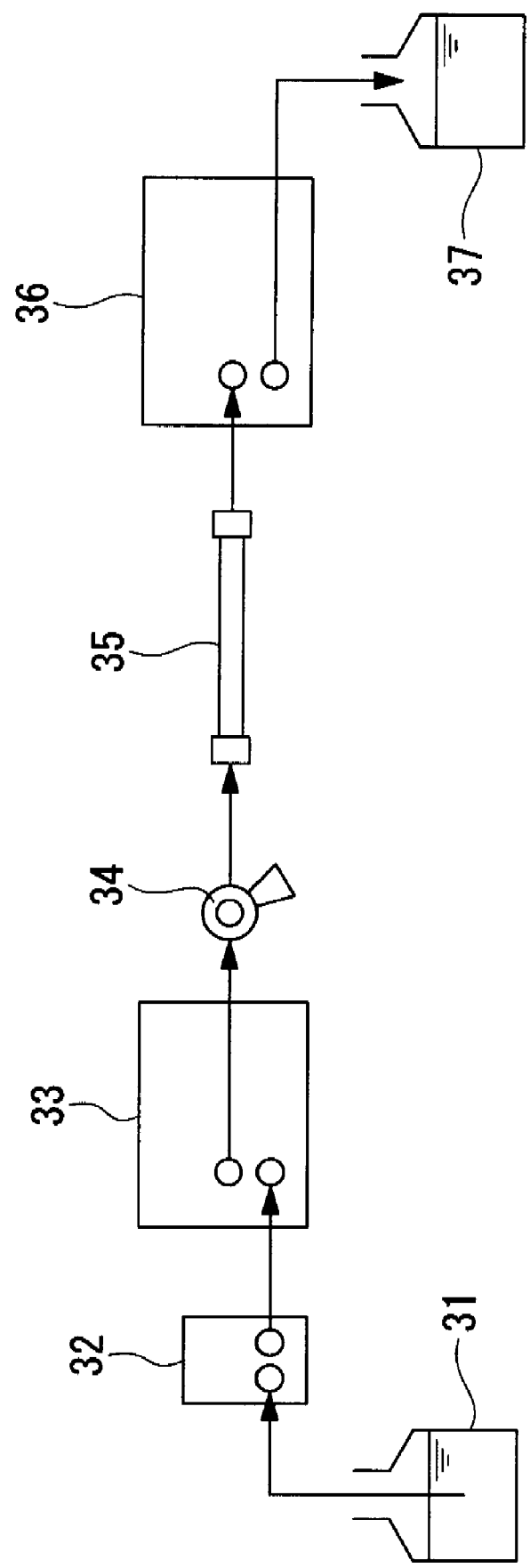
FIG. 6 is a schematic diagram showing construction of liquid chromatograph.

First, a liquid chromatography system used in this measurement is schematically shown in FIG. 6.

The liquid chromatographic measurer is constructed by being provided with a container 31 added with an eluent, a degasser 32 for degasing the eluent, a pump 33 for feeding the eluent, an injector 34 for injecting a sample into the eluent, a column 35 for separating a sample, a differential refractive index detector 36 for detecting the change of deflection angle on the basis of a refractive index difference between the sample liquid separated by the column 35 and a reference liquid, and a container for reserving a sample liquid outflowing from the differential refractive index detector 36.

In measurement by the above liquid chromatography system, water was used as the eluent, a sample with a predetermined concentration as a measurement object was injected into the eluent while feeding it at a flow rate of 1 mL/min. A ligand exchange & size separation-type column for sugar analysis (KS-801 made by Showa Denko K. K.) was used for the column 35, and the temperature of liquid in the column was maintained at 50° C.

Example 1

In Example 1, a measurement of chromatogram by the above liquid chromatography system was carried out by injecting 20 μL of a sucrose aqueous solution of 1.25 μg/μL into the solvent as sample and using a differential refractive index detector 36 provided with the flow cell 1 as shown in FIG. 4. The measurement results are shown in FIG. 7.

Comparative Example 1

Figure 5:
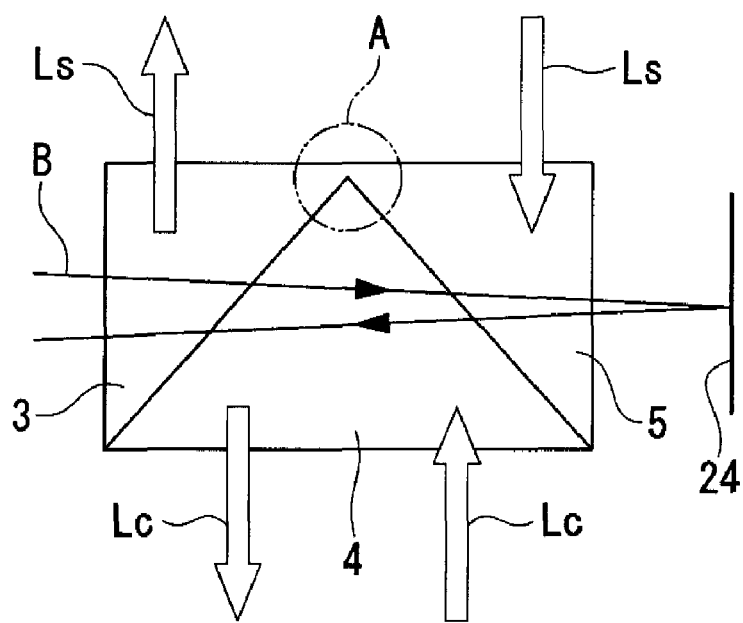
FIG. 5 is a schematic diagram for describing flow of sample liquid and reference liquid in conventional flow cell.

In Comparative example 1, a measurement of chromatogram by the above liquid chromatography system was carried out with the same sample as Example 1 except that a differential refractive index detector 36 was provided with the flow cell as shown in aforesaid FIG. 5. The measurement results are shown in FIG. 8.

Figure 7:
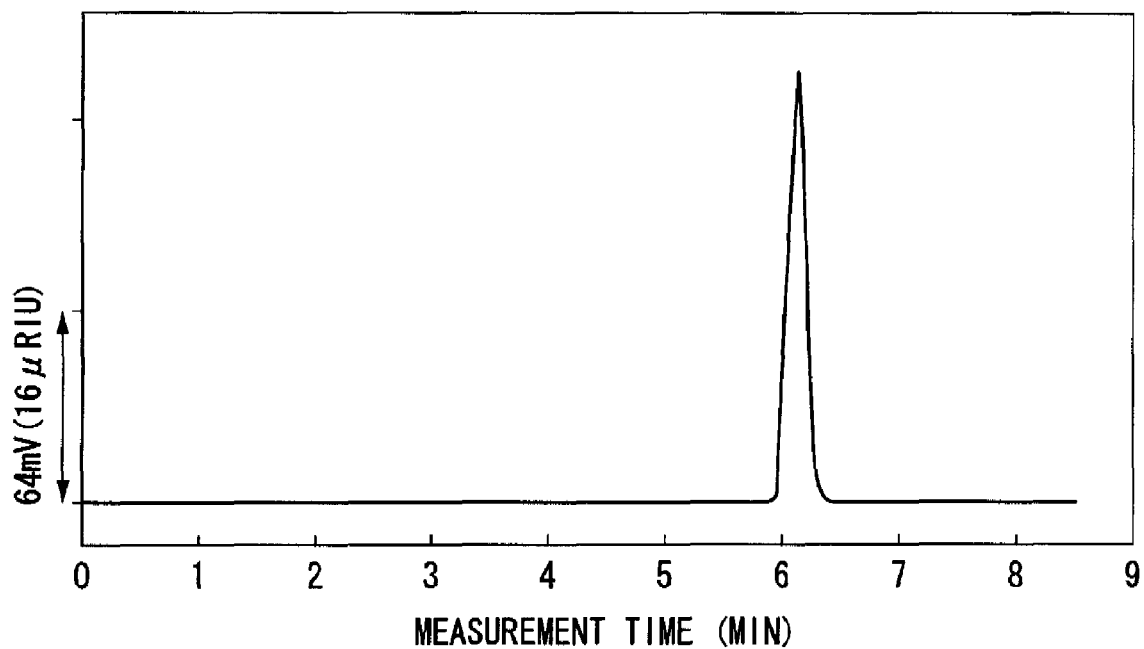
FIG. 7 is a chromatogram of Example 1.
Figure 8:
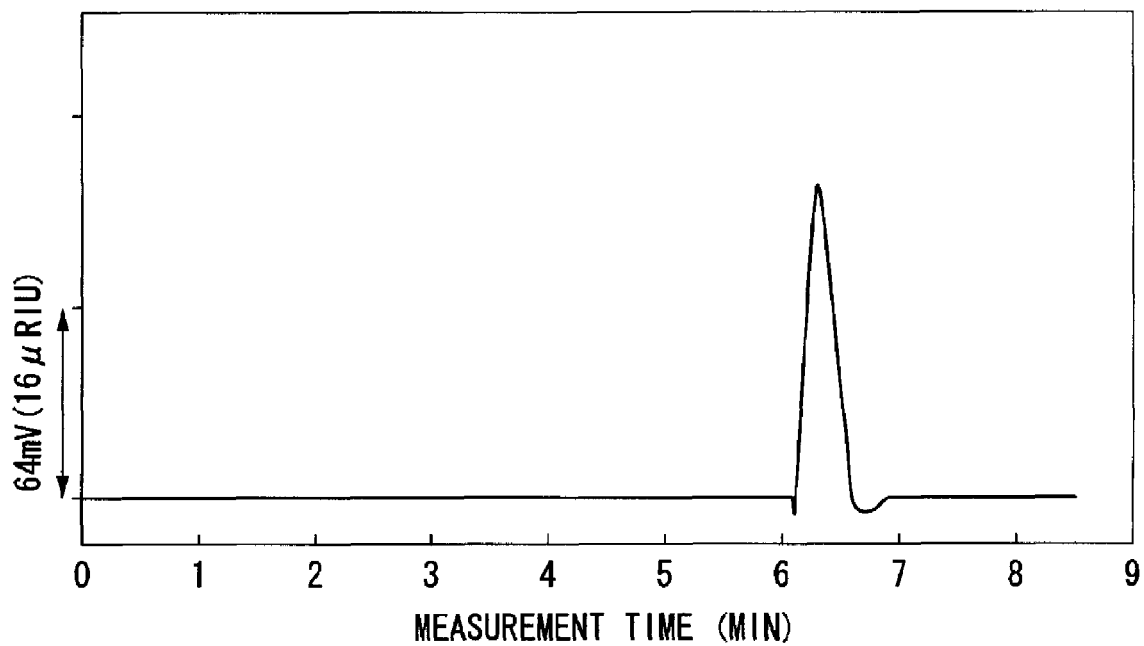
FIG. 8 is a chromatogram of Comparative example 1.

From the measurement results shown in FIG. 7 and FIG. 8, a peak in the chromatogram of Example 1 is sharper than in the chromatogram of Comparative example 1, a small peak of peak rising edge and a broad small peak of peak trailing edge are also not found. From the above, it is known that the differential refractive index detector of the present invention can be fully supplied for analysis using a high-performance column.

Example 2

In Example 2, a measurement of chromatogram by the above liquid chromatography system was carried out by injecting 20 μL of a aqueous solution including a sucrose and a fructose of 1 ng/μL respectively into the eluent as sample and using a differential refractive index detector 36 provided with the flow cell 1 as shown in FIG. 4. The measuring results are shown in FIG. 9.

Comparative Example 2

Figure 10:
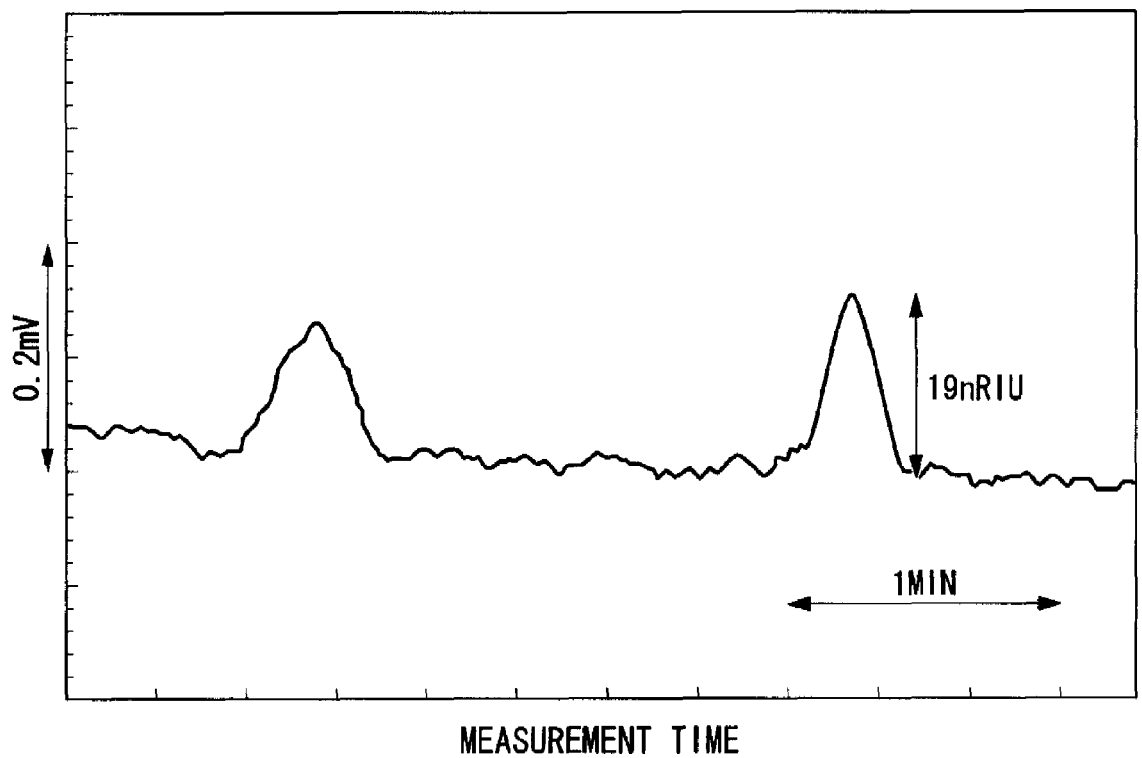
FIG. 10 is a chromatogram of Comparative example 2.
Figure 11A:
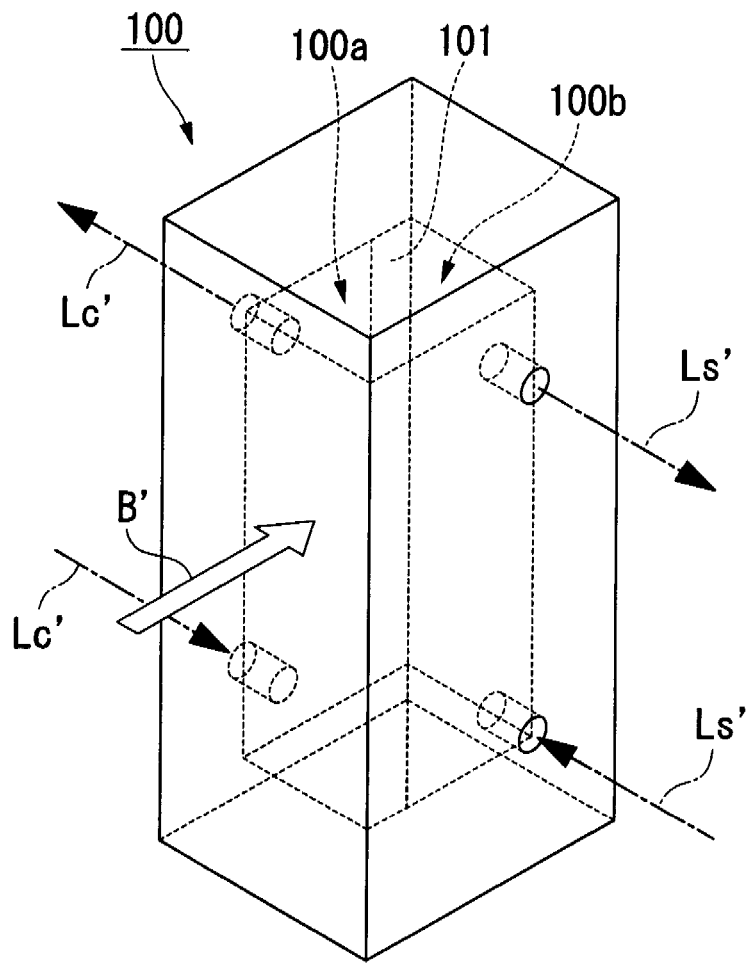
FIG. 11A is an oblique view showing structure of conventional flow cell.
Figure 11B:
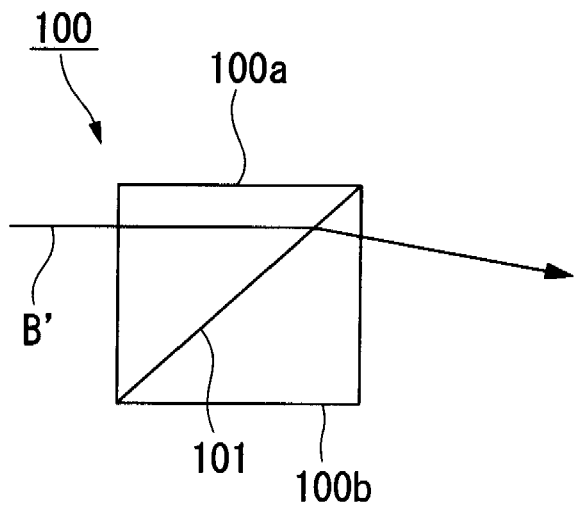
FIG. 11B is a schematic diagram showing a cross-section structure of conventional flow cell shown in FIG. 11A.

In Comparative example 2, a measurement of chromatogram by the above liquid chromatography system was carried out with the same sample as Example 2 except that a differential refractive index detector 36 provided with the flow cell as shown in FIG. 11A and FIG. 11B is used. The flow cell 100 has the same volume as that of the flow cell 1 used in Example 2. The measuring results are shown in FIG. 10. The word "nRIU" shown in FIG. 9 and FIG. 10 means a nano unit of refractive index difference.

Figure 9:
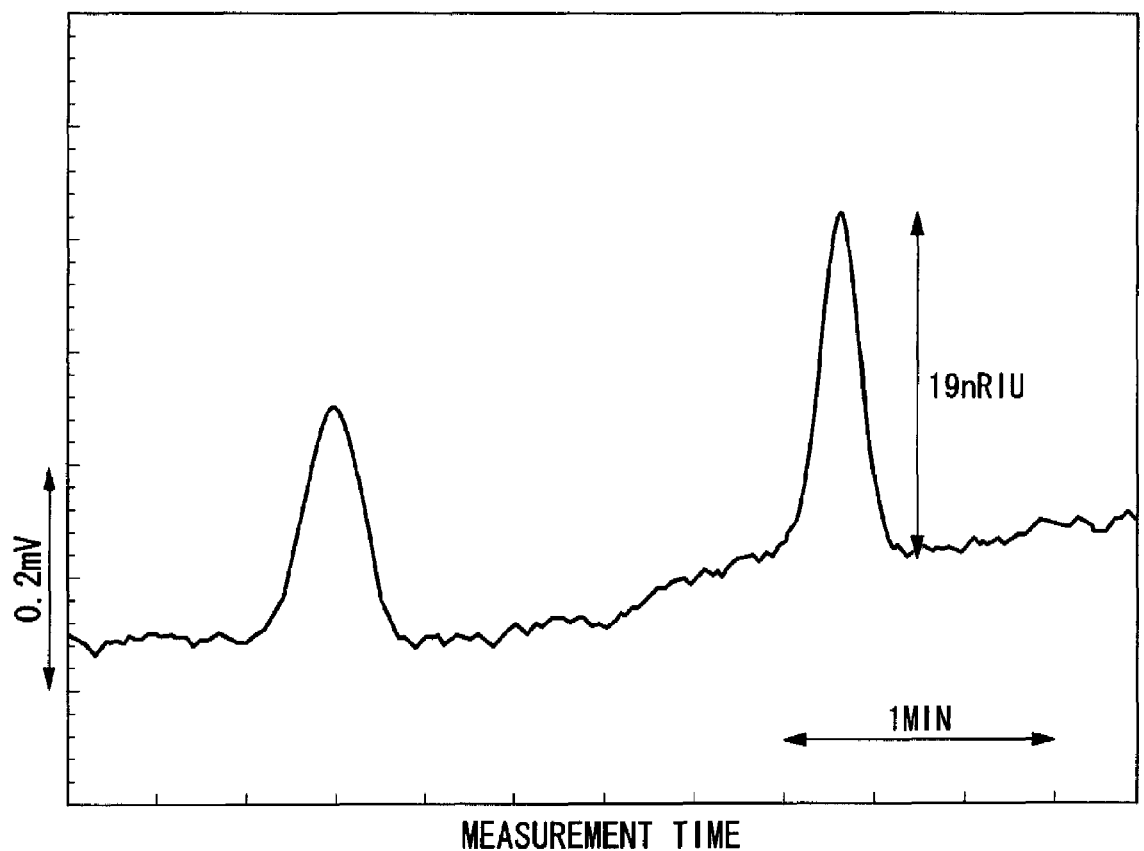
FIG. 9 is a chromatogram of Example 2.

From the measurement results shown in FIG. 9 and FIG. 10, a sucrose peak was detected after fructose in both the chromatograms of Example 2 and Comparative example 2, but the peak height of sucrose peak of Example 2 shows a nearly double value for Comparative example 2. Here, the samples of Example 2 and Comparative example 2 have the same concentration of sucrose solution, therefore the detected nRIU are also equal. So a sensitivity of detector of Example 2 is higher than that of Comparative Example 2. The S/N ratio of chromatogram of Example 2 in FIG. 9 was about 20, S/N ratio of chromatogram of Comparative example 2 in FIG. 10 was about 8.5, and the S/N ratio of Example 2 is greater than that of Comparative example 2. The noise was measured by a method according to ASTM (E685-79). From the above, it could be confirmed that high sensitivity was obtained by the differential refractive index detector of present invention, without broadening of the peak in analysis using a high-performance column.

INDUSTRIAL APPLICABILITY

As described above, the present invention enables measuring a change of the deflection angle at high sensitivity on the basis of the refractive index difference of a measurement beam transmitting a flow cell between a reference liquid and a sample liquid by improving the liquid replacement properties of the reference liquid and responding quickly to a refractive index change of the sample liquid.

The invention claimed is:

1. An apparatus for measuring a differential refractive index having a flow cell deflecting a measurement beam in accordance with the refractive index difference between a reference liquid and a sample liquid for measuring the change of the deflection angle on the basis of the refractive index difference of the measurement beam transmitted between the reference liquid and the sample liquid,
   wherein the flow cell comprises three independent chambers including a first chamber, a second chamber adjacent to the first chamber and a third chamber adjacent to the second chamber, and the measurement beam is irradiated on the flow cell so as to sequentially transmit these three chambers in a state in which the reference liquid flows or is sealed in the first and third chambers and in a state in which the sample liquid flows or is sealed in the second chamber;
   wherein the apparatus further comprises a flow passage which allow the reference liquid to flow from the first chamber to the third chamber;
   wherein the apparatus further comprises a first sealing plate forming the flow passages and a first block, wherein the first sealing plate is sandwiched between the first block and the flow cell;
   wherein the flow cell further comprises:
   a first inflow port allowing the reference liquid to flow into the first chamber,
   a first outflow port allowing the reference liquid to flow out from the first chamber,
   a second inflow port allowing the sample liquid to flow into the second chamber,
   a second outflow port allowing the sample liquid to flow out from the second chamber,
   a third inflow port allowing the reference liquid to flow into the third chamber, and
   a third outflow port allowing the reference liquid to flow out from the third chamber, wherein
      the first sealing plate comprises a reference-side inflow hole and a reference-side outflow hole in positions corresponding to the first inflow port and the third outflow port,
      the first block comprises a reference-side inflow passage and a reference-side outflow passage at positions corresponding to the reference-side inflow hole and the reference-side outflow hole, and
      the flow passage is formed between the first outflow port and the third inflow port; and
      wherein the apparatus further comprises:
   a second sealing plate having a sample-side inflow hole and a sample-side outflow hole at positions corresponding to the second inflow port and the second outflow port, and
   a second block having a sample-side inflow passage and a sample-side outflow passage in positions corresponding to the sample-side inflow hole and the sample-side outflow hole, wherein the second sealing plate is sandwiched between the second block and the flow cell.

2. An apparatus for measuring the differential refractive index according to claim 1, wherein the flow cell is rough quadrangular prism and the first to third chambers are rough triangular prism.

3. An apparatus for measuring the differential refractive index according to claim 1, wherein the flow cell has a first partition plate for partition between the first chamber and the second chamber and a second partition plate for partition between the second chamber and the third chamber, and the first partition plate and the second partition plate are arranged perpendicular to each other and each of the plates has an angle of 45±1° relative to a optical axis of the measurement beam.

4. A differential refractive index detector, comprising an apparatus for measuring the differential refractive index according to claim 1,
   a light emitting device emitting a measurement beam on the apparatus for measuring the differential refractive index, and
   a photo-detection device detecting the measurement beam that transmits the apparatus for measuring the differential refractive index.

5. A differential refractive index detector according to claim 4, further comprises a light reflection device that reflects the measurement beam emitted by the light emitting device and transmitting the flow cell in the order of the first, second and third chambers so as to transmit the flow cell in the order of the third, second and first chambers,
   wherein the photo-detection device detects measurement beam reflected by the light reflection device and transmitted through the flow cell.

6. A method for measuring the differential refractive index using the apparatus for measuring the differential refractive index according to claim 1, comprises
   sealing or making flowing the reference liquid in the first and third chambers,
   sealing or making flowing the sample liquid flows in the second chamber,
   irradiating a measurement beam on the flow cell so as to sequentially transmit the three chambers, and
   measuring a change of the deflection angle on the basis of a refractive index difference of the measurement beam transmitted the flow cell between the reference liquid and the sample liquid.

\* \* \* \* \*